(12) United States Patent
Doughty et al.

(10) Patent No.: US 8,728,096 B2
(45) Date of Patent: May 20, 2014

(54) LIGATING BAND DISPENSER WITH A SLIDING DEPLOYMENT SYSTEM

(75) Inventors: Marshal Doughty, Quincy, MA (US); Michael Abi-Kheirs, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 827 days.

(21) Appl. No.: 11/839,220

(22) Filed: Aug. 15, 2007

(65) Prior Publication Data
US 2008/0097478 A1    Apr. 24, 2008

Related U.S. Application Data

(60) Provisional application No. 60/853,767, filed on Oct. 24, 2006.

(51) Int. Cl.
*A61B 17/10* (2006.01)
(52) U.S. Cl.
USPC .......................................................... 606/140
(58) Field of Classification Search
USPC ......... 606/140, 141, 139, 151, 153–158, 142, 606/113; 600/129, 127, 112, 104; 128/830, 128/842; 433/23
See application file for complete search history.

(56) References Cited

U.S. PATENT DOCUMENTS

| | | | |
|---|---|---|---|
| 5,269,789 A | 12/1993 | Chin et al. | |
| 5,356,416 A | 10/1994 | Chu et al. | |
| 5,398,844 A | 3/1995 | Zaslavsky et al. | |
| 5,569,268 A * | 10/1996 | Hosoda .......................... | 606/140 |
| 5,624,453 A | 4/1997 | Ahmed | |
| 5,853,416 A | 12/1998 | Tolkoff | |
| 5,857,585 A | 1/1999 | Tolkoff et al. | |
| 5,913,865 A | 6/1999 | Fortier et al. | |
| 6,007,551 A | 12/1999 | Peifer et al. | |
| RE36,629 E | 3/2000 | Zaslavsky et al. | |
| 6,235,040 B1 | 5/2001 | Chu et al. | |
| 6,585,642 B2 * | 7/2003 | Christopher ................... | 600/156 |
| 6,676,672 B2 * | 1/2004 | Chu et al. ....................... | 606/139 |
| 7,815,565 B2 * | 10/2010 | Stefanchik et al. ........... | 600/121 |
| 2001/0014810 A1 * | 8/2001 | Chu et al. ....................... | 606/139 |
| 2002/0072757 A1 | 6/2002 | Ahmed et al. | |
| 2004/0006256 A1 | 1/2004 | Suzuki et al. | |

FOREIGN PATENT DOCUMENTS

DE    29709170    6/1998

OTHER PUBLICATIONS

International Search Report & Written Opinion, PCT/US2007/019386, Apr. 14, 2008.
International Preliminary Report on Patentability with Written Opinion, from PCT/US2007/019386, mailed May 7, 2009.

* cited by examiner

*Primary Examiner* — Corrine M McDermott
*Assistant Examiner* — Christopher L Templeton
(74) *Attorney, Agent, or Firm* — Fay Kaplun & Marcin, LLP

(57) ABSTRACT

A ligating band dispenser for attachment to an endoscope having sliding elements that are positioned on the outer surface of a support structure of the ligating band dispenser. The sliding elements may be slidably engaged to the support structure. For example, the sliding elements may slide along a groove on the outer surface of the support structure. The sliding elements are advanced forward along the groove, causing the sliding elements to impact a ligating band and push the ligating band forward until it is deployed off the dispenser.

23 Claims, 12 Drawing Sheets

LIGATING BAND DISPENSER WITH A SLIDING DEPLOYMENT SYSTEM

CROSS-REFERENCE TO RELATED APPLICATIONS

This application claims priority to provisional application Ser. No. 60/853,767 (filed 24 Oct. 2006), which is incorporated by reference herein.

TECHNICAL FIELD

The present invention relates to medical ligating instruments and more particularly to medical ligating instruments that dispense ligating bands.

BACKGROUND

Ligation is a medical procedure whereby the physician ties off or mechanically constricts a piece of body tissue with an encircling ligature such as a suture, clip, or elastic band. The purpose of ligation is to impede or obstruct the flow of blood, fluids, and other bodily materials through the tissue. For example, the physician can remove target tissue by ligating it to obstruct all circulation through the target tissue, thereby causing the tissue to die and slough off.

For ligating tissue inside a body cavity, orifice, or lumen, physicians often use an endoscope to access the target tissue and ligate it. In one such form of endoscopic ligation, the physician uses the endoscope to position a stretched elastic band over the target tissue and then release the band onto the tissue so that the band contracts and catches the tissue. The inward pressure of the elastic band constricts the target tissue.

Ligating instruments have been the subject of a number of patents, including U.S. Pat. No. 5,269,789 to Chin et al.; U.S. Pat. No. 5,356,416 to Chu et al.; U.S. Pat. No. 5,398,844 to Zaslavsky et al.; U.S. Pat. No. 5,857,585 to Tolkoff et al.; U.S. Pat. No. 5,853,416 to Tolkoff; U.S. Pat. No. 5,913,865 to Fortier et al.; U.S. Pat. No. 6,235,040 to Chu et al.; and U.S. Pat. No. RE 36,629 to Zaslavsky et al. The disclosures of these prior U.S. patents are expressly incorporated by reference herein.

A number of ligating instruments have been developed to sequentially deploy multiple ligating bands. Many such ligating instruments, such as the one disclosed in U.S. Pat. No. 5,857,585 to Tolkoff et al., rely on a trigger wire which is sequentially looped around each ligating band and over the distal edge of the dispenser. Thus, the process of manufacturing such ligating band dispensers involves the steps of sequentially weaving the wire around each ligating band and over the distal edge of the dispenser.

SUMMARY OF THE INVENTION

In one aspect, the present invention provides a ligating band dispenser comprising: a support structure having a channel, an outer surface, a proximal end, and a distal end; at least one sliding element positioned on the outer surface of the support structure; a pull line engaged with the at least one sliding element; and at least one ligating band positioned on the outer surface of the support structure distal to at least one sliding element; wherein pulling the pull line causes at least one sliding element to move distally with respect to the outer surface of the support structure, thereby causing at least one ligating band to move distally with respect to the outer surface of the support structure and off of the distal end of the support structure.

In another aspect, the present invention provides a ligating band dispenser comprising: (a) a support structure having a channel, a proximal end, a distal end, an outer surface, and at least one slide path on the outer surface; (b) at least one ligating band positioned on the outer surface of the support structure; (c) a pull line adapted to be pulled proximally for deploying the at least one ligating band off of the distal end of the support structure; and (d) a means for moving the at least one ligating band distally, wherein the means for moving the at least one ligating band distally moves along the at least one slide path.

In another aspect, the present invention provides a device for deploying a ligating band, comprising: a support structure; a pushing element positioned on the outer surface of the support structure; an actuating element for moving the pushing element; and a ligating band seated adjacent to the pushing element; wherein actuation of the actuating element causes the pushing element to push against the ligating band and move the ligating band distally along the support structure.

In another aspect, the present invention provides a method of dispensing ligating bands, comprising the steps of: (a) providing a ligating dispenser device comprising: (i) a support structure having a channel, an outer surface, a proximal end, and a distal end; (ii) at least one sliding element positioned on the outer surface of the support structure; (iii) a pull line engaged with the at least one sliding element; and (iv) at least one ligating band positioned on the outer surface of the support structure distal to at least one sliding element; and (b) pulling the pull line proximally, thereby causing at least one sliding element to move distally with respect to the outer surface of the support structure, thereby causing at least one ligating band to move distally with respect to the outer surface of the support structure and off of the distal end of the support structure.

DETAILED DESCRIPTION

Figure 1:
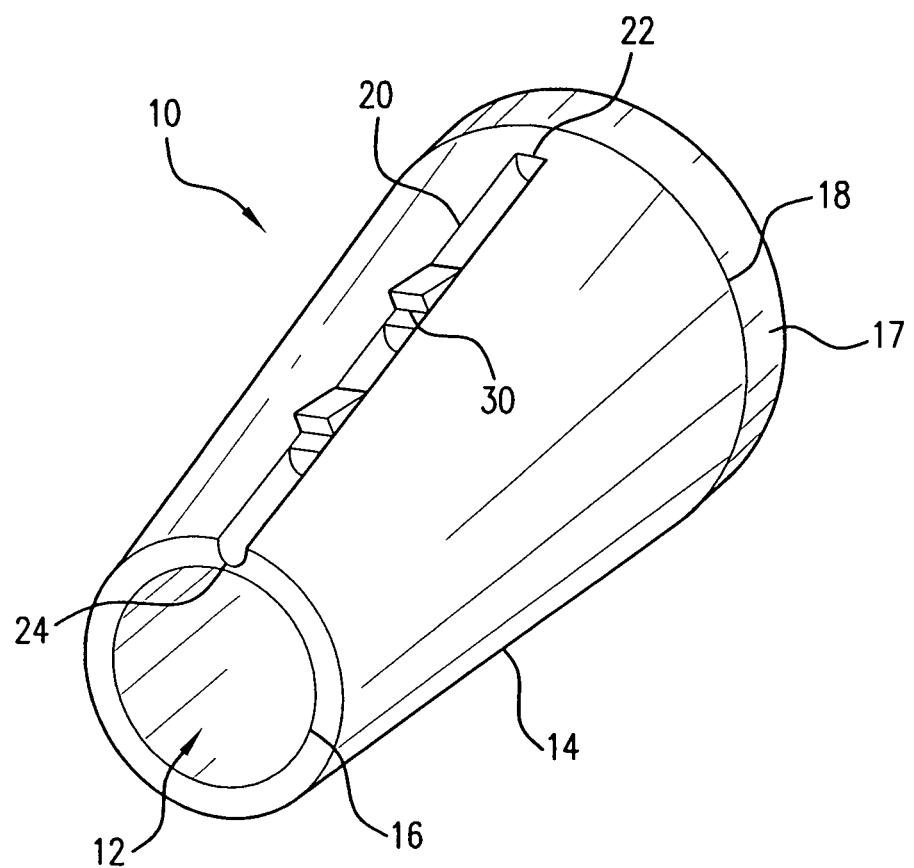
FIG. 1 is a perspective view of a ligating band dispenser according to a first embodiment (shown without the ligating bands).
Figure 2:
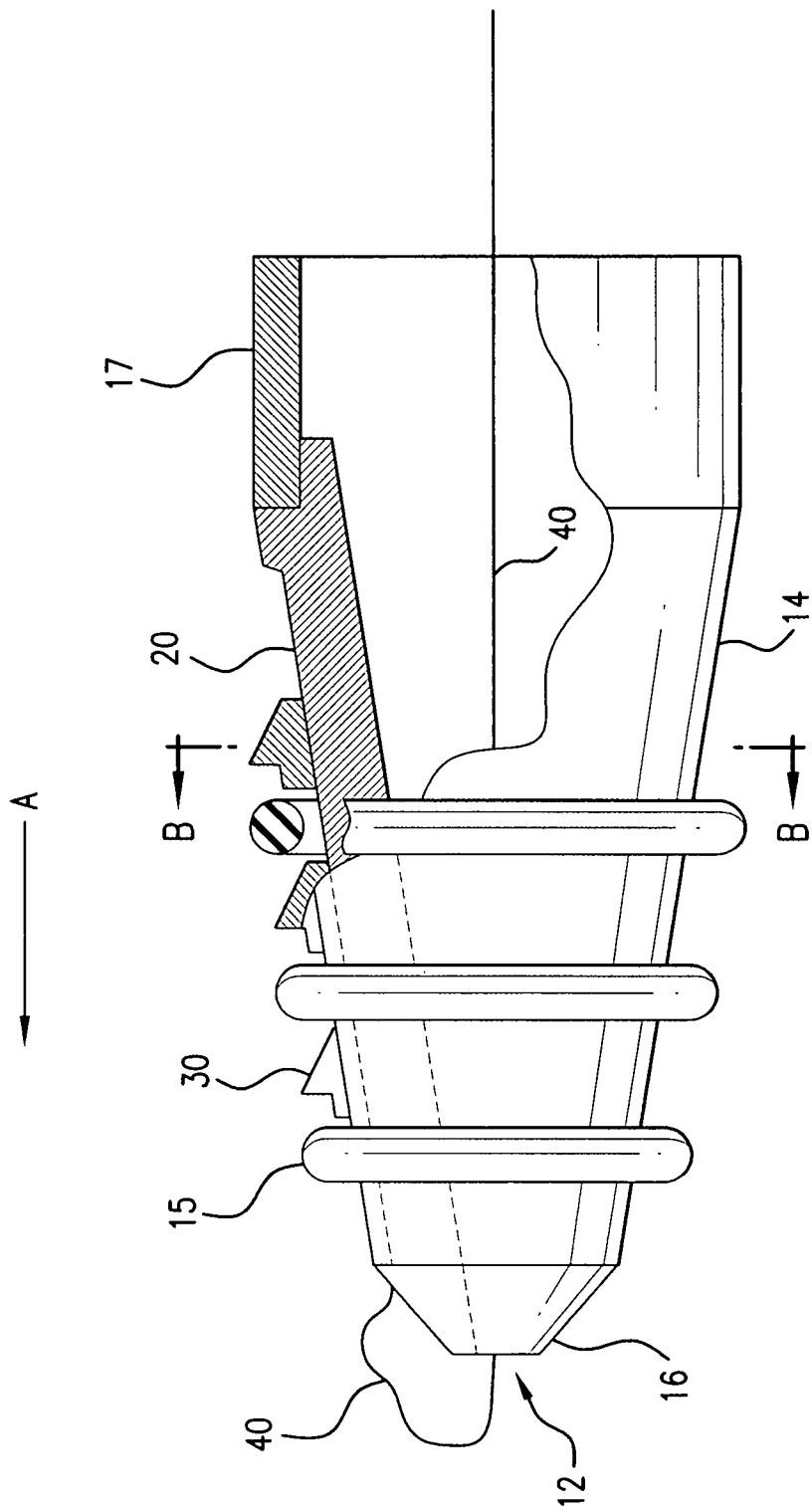
FIG. 2 is a longitudinal cross-section view of the ligating band dispenser of FIG. 1.

As illustrated in FIGS. 1 and 2, a ligating band dispenser 10 according to a first embodiment includes a substantially cylindrical housing or support structure 14 which has a central bore or channel 12 extending axially through the support structure 14. The central channel 12 is wide enough to accept tissue into the channel and allow visualization through it, for example when the dispenser is attached to the end of an endoscope. In this embodiment, the dispenser 10 includes a flexible connector 17 which allows the dispenser 10 to be attached to the distal tip of an endoscope. A plurality of elastic ligating bands 15 are received in a stretched condition around the support structure 14.

On the outer surface of the support structure 14 is a slide path, which in this embodiment is a groove 20 that extends from a proximal point 22 on the support structure 14 to a distal point 24 on the support structure 14. In this embodiment, the groove 20 begins at a point close to the proximal edge 18 of the support structure 14 and extends to the distal edge 16 of the support structure 14.

Figure 3:
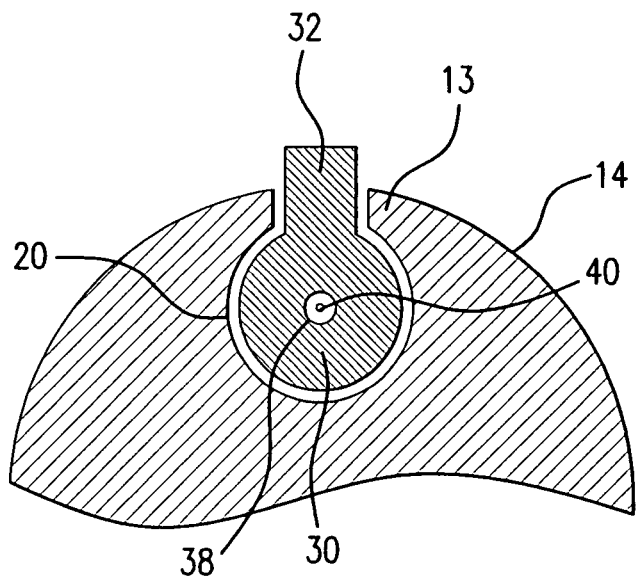
FIG. 3 is a fragmentary cross-section view of the ligating band dispenser of FIG. 2 taken along line B-B.
Figure 4:
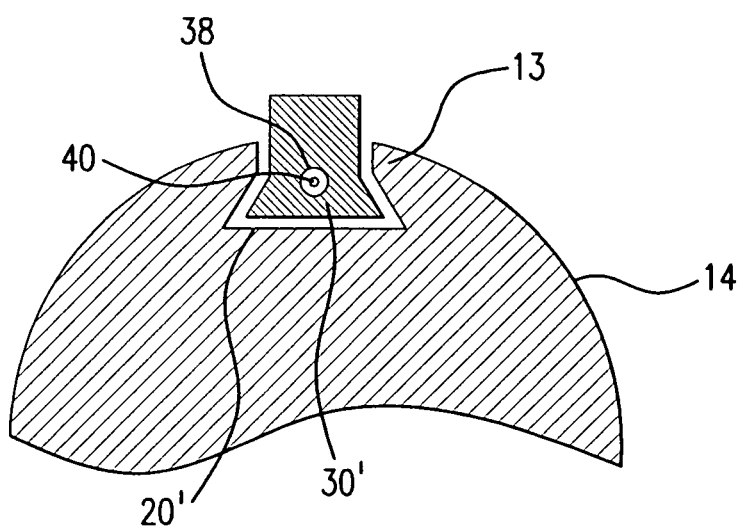
FIG. 4 is a fragmentary view of an alternate embodiment of the ligating band dispenser of the present invention shown in cross-section taken along a line similar to line B-B in FIG. 2.

The groove 20 engages one or more slidable displacement members or sliding elements 30 that are slidable within the groove 20. The groove 20 and sliding elements 30 are adapted so that the groove 20 retains the sliding elements 30 within the groove while the sliding elements 30 slide within the groove 20. As illustrated in FIG. 3, in this first embodiment, the groove 20 and the associated portions of the sliding elements 30 are substantially in the shape of a right circular cylinder, and the groove 20 includes a shoulder 13 which retains the sliding elements 30 within the groove 20. In alternate embodiments, the groove and sliding elements may take other shapes or dimensions that allow the sliding elements to slide within the groove while being retained within the groove. For example, as illustrated in FIG. 4, the groove 20' and the associated portion of the sliding element 30' may take a substantially triangle-shaped geometry. In other embodiments, the slide path may be any other type of path upon or within which the sliding elements may slide, such as tracks, rails, or gutters.

In some embodiments, the outer surface of the support structure 14 may also have circumferential furrows (not shown) extending fully or partially around support structure 14. These circumferential furrows may serve to help seat the ligating bands onto the support structure 14.

Figure 5:
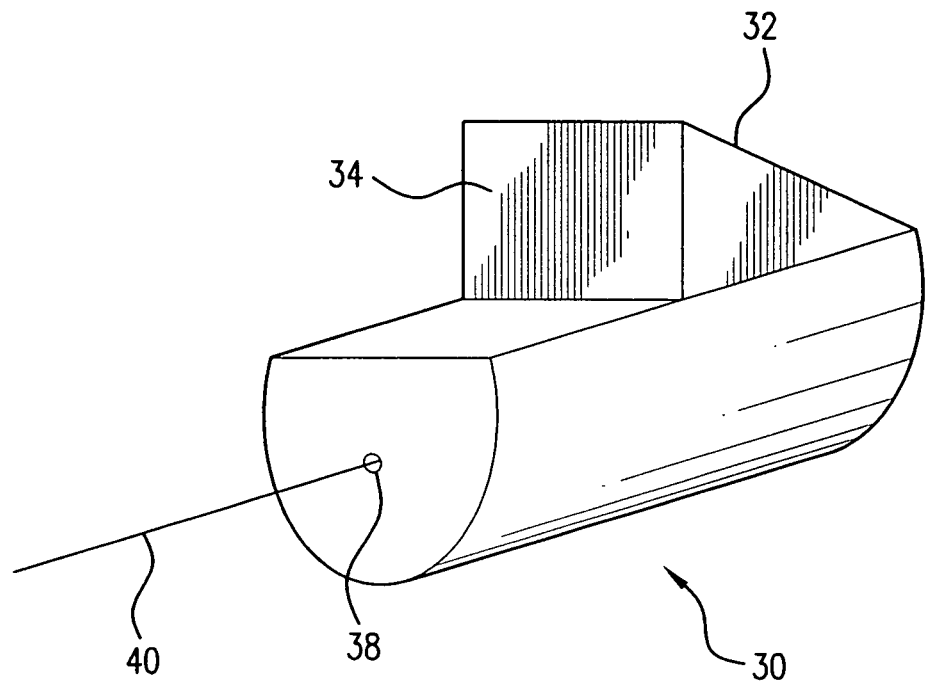
FIG. 5 is a perspective view of an embodiment of a sliding element.

Referring to FIGS. 3 and 5, in this first embodiment, the sliding elements 30 include a projecting element 32 that projects outwardly away from the outer surface of the support structure 14. The projecting element 32 provides an impacting surface 34 that impacts a ligating band 15 and urges the ligating band forward (distally) in the direction of arrow A (shown in FIG. 2). In alternate embodiments, the sliding elements 30 do not include a separate impacting surface on a projecting element. Rather, the body of such a sliding element may itself be adapted and sized to provide an impacting surface that impacts a ligating band, urging the ligating band forward.

Figure 6:
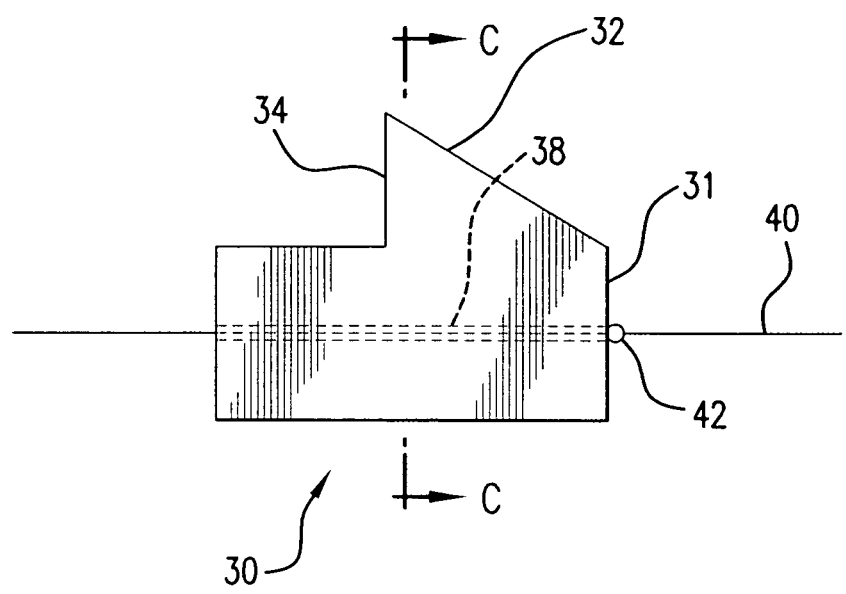
FIG. 6 is a side view of the sliding element of FIG. 5.

The sliding elements 30 are adapted to be advanced forward (distally, in the direction of arrow A shown in FIG. 2) as a pull line 40 is pulled. Referring to FIGS. 5 and 6, in this first embodiment, the pull line 40 travels through the sliding elements 30 via a lumen or channel 38 that extends axially within the sliding element. The pull line 40 has an engagement element such as a projection or knot 42 (seen in FIG. 6) that impacts the posterior (proximal) side 31 of the sliding element 30. In the illustrated embodiment, the knot 42 is larger than the width of the channel 38 so that the knot 42 cannot be pulled through the channel 38 and instead advances the sliding element 30.

Figure 7:
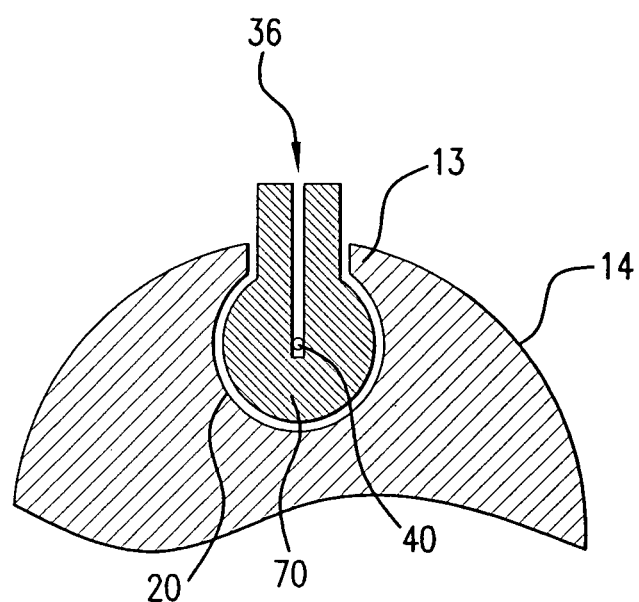
FIG. 7 is a fragmentary view of an alternate embodiment of a ligating band dispenser shown in cross-section taken along a line similar to line B-B in FIG. 2.

In alternate embodiments, the sliding elements may be adapted to easily separate from the pull line. For example, FIG. 7 illustrates an embodiment where the sliding element 70 has a slot 36 instead of a channel through which the pull line 40 travels. The slot 36 is open on one face of the sliding element 70 to facilitate assembly of the sliding element 70 and the pull line 40 or to facilitate disengagement of the sliding element 70 from the pull line 40. In other alternate embodiments, the pull line 40 is connected to the sliding elements by any of a number of attachment means, including tying, clamping, gluing or fastening. The pull line 40 may be a thread, filament, wire, or string.

Figure 8:
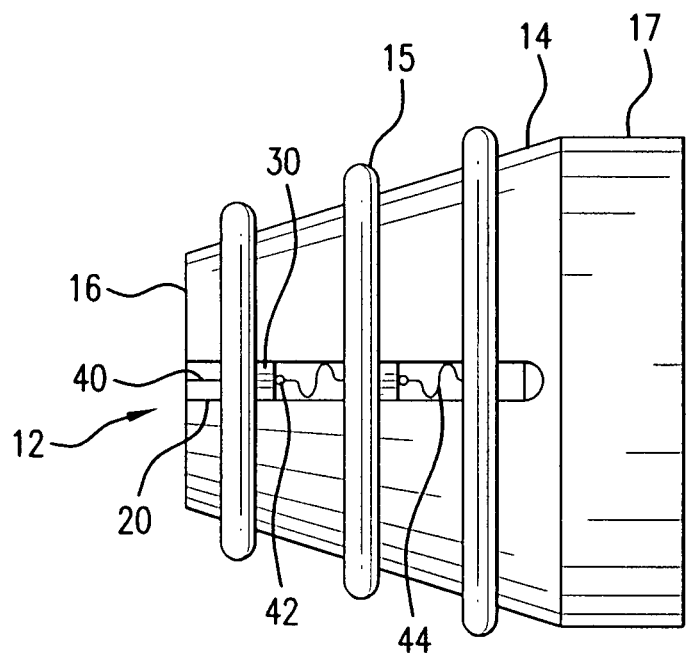
FIG. 8 is a top view of the ligating band dispenser of FIG. 1 (shown with the ligating bands).

As illustrated in FIG. 8, in this first embodiment, slack is introduced in the pull line by slack loops or bends 44. The slack bends 44 are coiled in the space between each sliding element 30. In an alternate embodiment, the slack bends 44 may be wedged in the space between one or more ligating bands and the outer surface of support structure 14. One of skill in the art will appreciate that the slack bends 44 can be positioned or arranged in any of a number of positions or arrangements designed to store the slack bends without interfering with the functioning of the ligating band dispenser. Initial pulling of the pull line 40 draws up the slack so that the pull line becomes taut and further pulling of the pull line 40 will begin advancing the attached sliding element 30 forward (distally). The slack in the pull line 40 allows each sliding element 30 to be advanced at intervals without moving other trailing sliding elements simultaneously.

Figure 9:
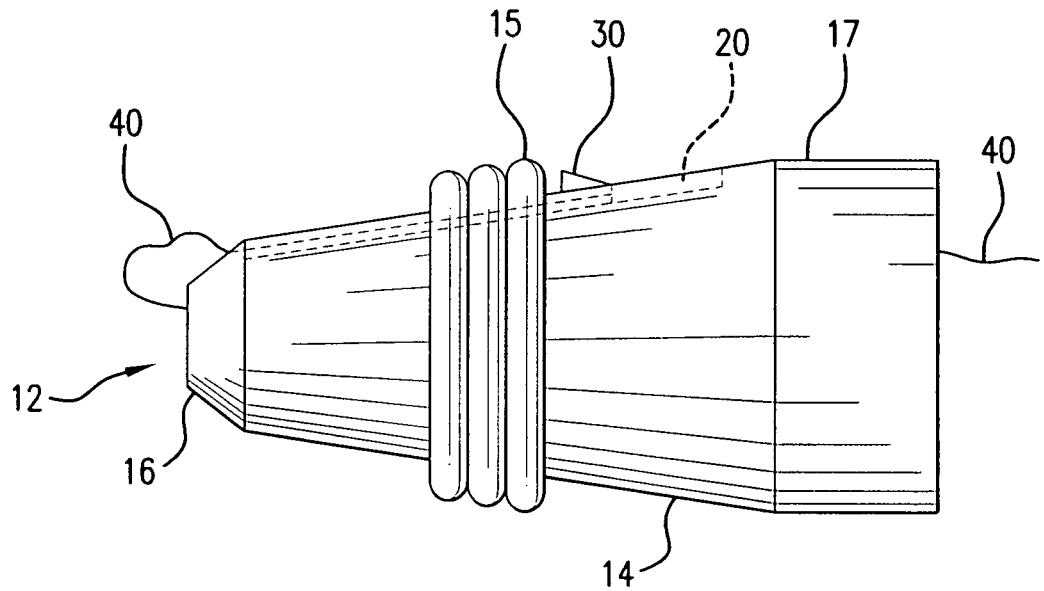
FIG. 9 is a side view of another alternate embodiment of a ligating band dispenser.

Referring again to FIG. 2, in this first embodiment, a sliding element 30 is positioned behind (proximal to) each of the ligating bands 15. In operation, the user actuates the ligating band dispenser 10 by pulling on the pull line 40. This may be done by an actuator or other means known in the art. After slack is drawn up, the pull line 40 advances a sliding element 30, causing the sliding element 30 to impact a ligating band 15, and urging the ligating band forward (distally) until the ligating band is released from the distal edge 16 of the support structure 14. In alternate embodiments, the sliding elements 30 may be positioned behind more than one ligating band 15. In one such embodiment, as shown in FIG. 9, each groove 20 on the support structure 14 may engage only a single sliding element 30. Thus, instead of having a plurality of sliding elements, with each one being positioned behind (proximal to) each ligating band, a single sliding element 30 is positioned behind all the ligating bands 15. In operation, pulling of the pull line 40 draws the sliding element 30 forward (distally), which then simultaneously urges all the ligating bands 15 forward (distally) so that are deployed sequentially, in intervals, as the pull line 40 continues to be pulled.

Figure 10:
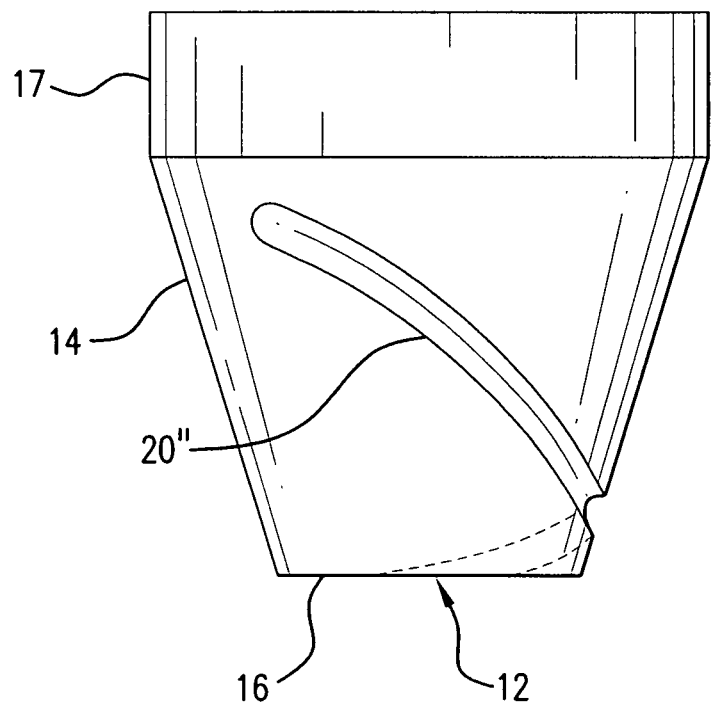
FIG. 10 is a top view of another alternate embodiment of a ligating band dispenser (shown without the ligating bands or sliding elements).

In the first embodiment, the groove 20 travels linearly and parallel to the axis of the support structure 14. In alternate embodiments, the groove travels at an oblique angle or helically with respect to the axis of the support structure 14. For example, as illustrated in FIG. 10, the groove 20" may travel in a corkscrew-like pattern from a proximal point on the support structure 14 to a distal point on the support structure 14.

Figure 11:
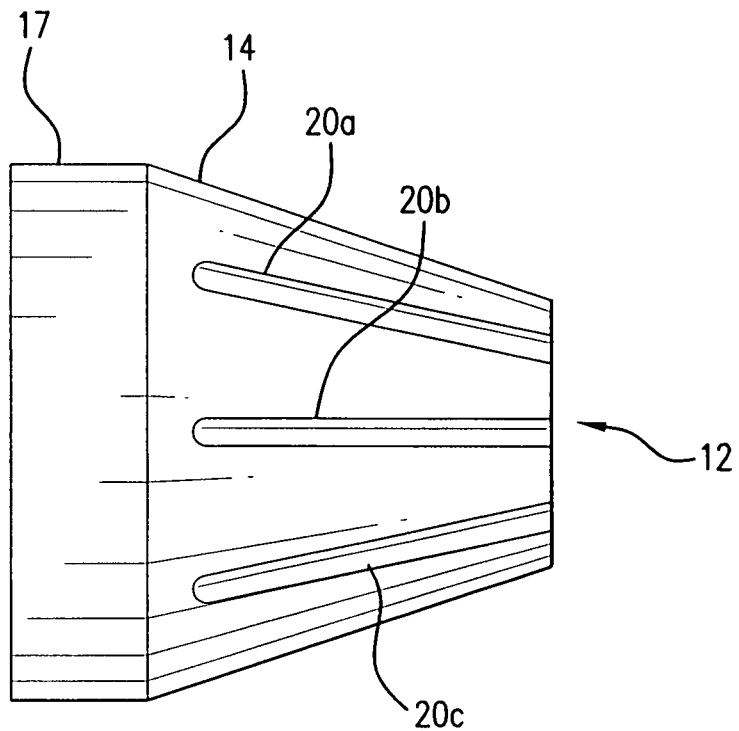
FIG. 11 is a top view of another alternate embodiment of a ligating band dispenser (shown without the ligating bands or sliding elements).

In this first embodiment, the support structure 14 includes a single groove 20. In alternate embodiments, the support structure 14 may include a plurality of grooves. For example, FIG. 11 illustrates an embodiment in which the ligating band dispenser 10 has three grooves 20a-20c. In this embodiment, each groove 20a-20c is engaged to its own set of sliding elements (not shown). In another example, two grooves may be positioned on opposite sides of the support structure with each groove having its own set of sliding elements. In operation, each ligating band is urged forward by the simultaneous advancement of the pair of oppositely-positioned sliding elements to facilitate symmetrical displacement of the ligating bands.

Figure 12:
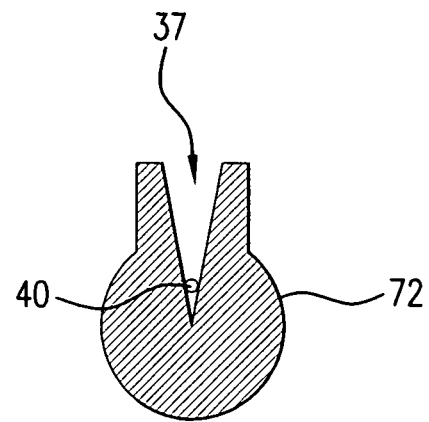
FIG. 12 is a cross-section view of an alternate embodiment of a sliding element taken along a line similar to line C-C in FIG. 6.

Once the ligating band is deployed, the subsequent disposition of the sliding element will vary according to the design of the ligating band dispenser. In certain embodiments, such as in the first embodiment shown in FIG. 2, the sliding element 30 disengages from the groove 20 as the sliding element is drawn past the distal edge 16 of the support structure 14. Within certain embodiments, where the sliding element is adapted to separate from the pull line (as previously described), the sliding element will dislodge from the pull line and be deposited in the body. Depending upon its design, the sliding element may spontaneously dislodge from the pull line after disengaging from the groove on the support structure, or the sliding element may be caused to dislodge by agitation induced by such acts as manipulation of the pull line, or such events as the sliding element colliding against a part of the ligating band dispenser or endoscope. For example, as shown in FIG. 12, the sliding element 72 may be designed with a V-shaped slot 37 such that the sliding element spontaneously separates from the pull line 40 after the sliding element 72 disengages from the groove on the support structure.

In certain embodiments, the ligating band dispenser is adapted to rotate the sliding element as it moves distally along the support structure. This rotation may serve various functions, including allowing the pull line to disengage from the sliding element, or reducing the sliding element's outward projection from the surface of the support structure. In some cases, the rotation is initiated after the sliding element deploys a ligating band. For example, referring to FIG. 14, a sliding element 76 may rotate as shown in the progression from frame A to B to C, causing sliding element 76 to release the pull line 40.

Figure 14A:
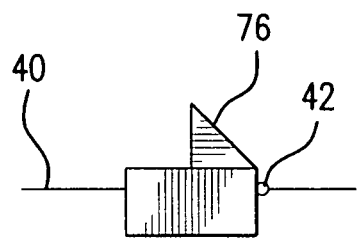
FIGS. 14A-C are side views of a sliding element according to another embodiment (shown as it rotates forward).
Figure 14B:
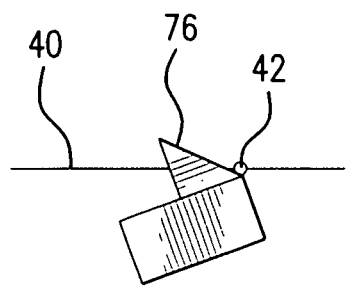
Figure 14C:
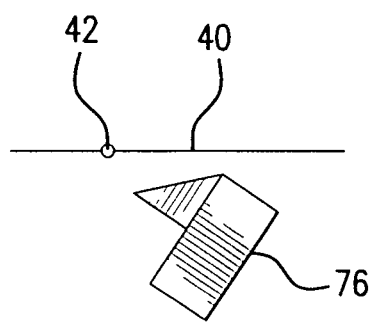

In another example, as shown in FIG. 14, the ligating band dispenser may be designed such that the slotted sliding element rotates forward after deploying a ligating band. As illustrated in the progression from FIGS. 14A to 14B to 14C, the pull line disengages from the sliding element as the sliding element rotates forward.

In some embodiments where the sliding element dislodges from the pull line after deployment of the ligating band, the sliding element may be shaped or dimensioned to be retrieved by the operator by one or more of various means. For example, the sliding element can be shaped and dimensioned to allow vacuum suction or forceps retrieval through the lumen of an endoscope.

In other embodiments where the sliding element dislodges from the pull line, the sliding element may be designed to be eliminated through the digestive tract. In such embodiments, the sliding element may be shaped and dimensioned to avoid causing obstructions as it travels through the digestive tract.

In yet other embodiments where the sliding element dislodges from the pull line, the sliding element may be designed to degrade within the body and/or be absorbed by the body. For example, the sliding element may be formed of biodegradable polymers such as polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L-lactide), poly(lactic acid-co-glycolic acid), 50/50 (D,L-lactide-co-glycolide); polydioxanone; polypropylene fumarate; polydepsipeptides; polycaprolactone and co-polymers and mixtures thereof such as poly(D, L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing.

In another embodiment of the present invention, the sliding element does not dislodge from the pull line after deployment of a ligating band. Rather, the sliding element continues to be drawn by the pull line and is retracted inside the central channel 12 of the support structure 14 and then, optionally, through the lumen of the endoscope (not shown).

Figure 13:
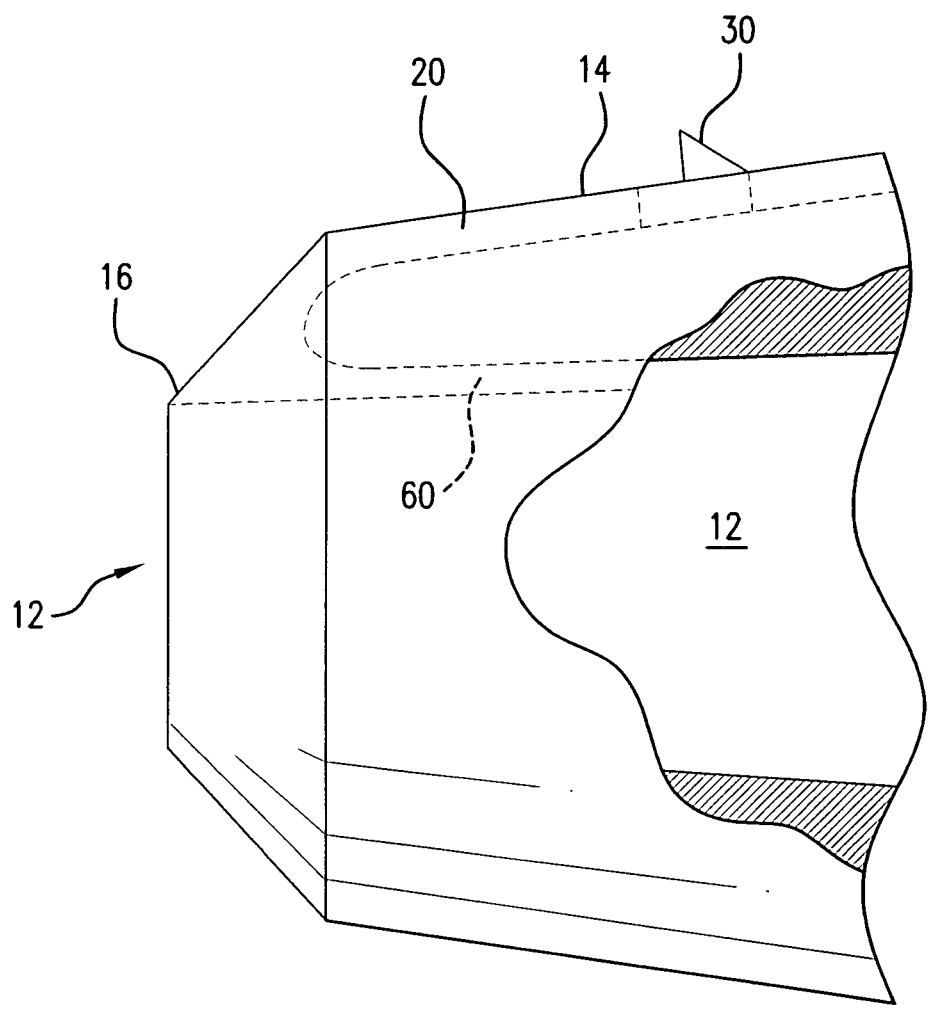
FIG. 13 is a fragmentary side view of an alternate embodiment of a ligating band dispenser shown partially in longitudinal cross-section.

In an alternate embodiment, as illustrated in FIG. 13, the support structure 14 includes a groove 60 on the inner surface that is continuous with the groove 20 on the outer surface. The inner groove 60 extends from a distal point on the inner surface of the support structure 14 to a proximal point on the inner surface of the support structure 14. In operation, after the sliding element 30 deploys a ligating band (not shown) and is drawn past the distal edge 16 of the support structure, the sliding element 30 continues to be engaged to the support structure via the inner groove 60. The sliding element may then be retracted through the lumen of an endoscope or be dislodged from the pull line.

Figure 15:
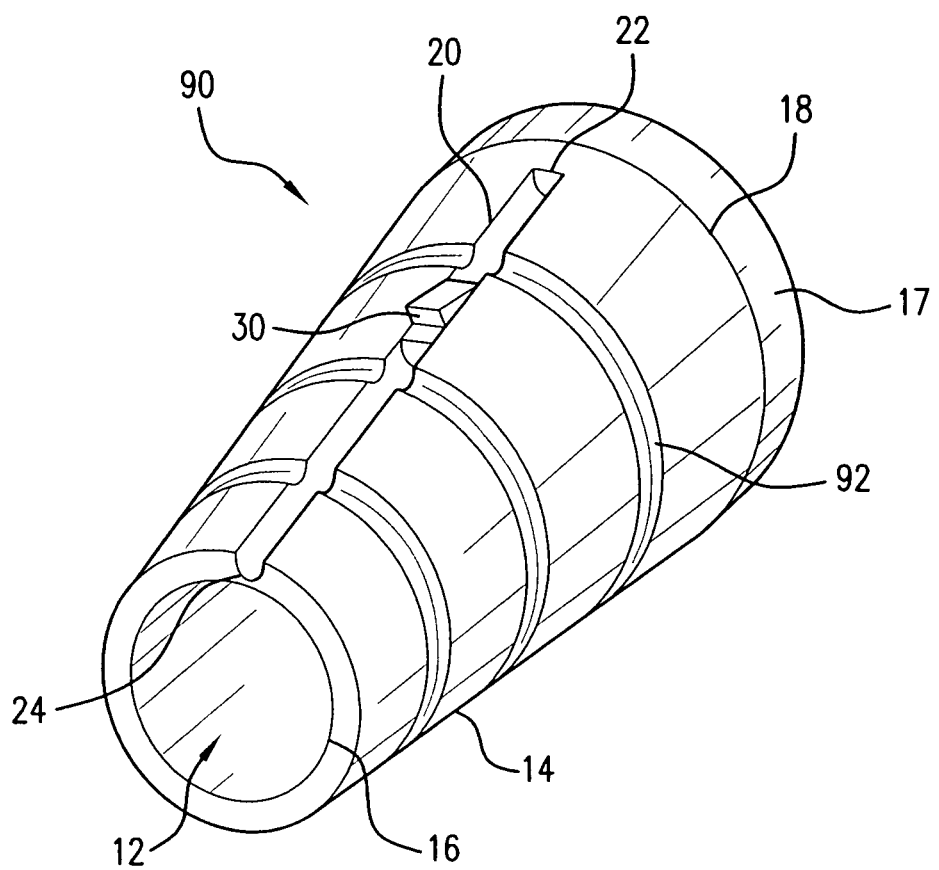
FIG. 15 is a perspective view of a ligating band dispenser according to another embodiment.

In yet another embodiment of the present invention, as illustrated in FIG. 15 for ligating band dispenser 90, only a single sliding element 30 is situated proximal to all the ligating bands (not shown). The support structure 14 has a series of circumferential furrows 92 extending fully or partially around support structure 14. These circumferential furrows 92 may serve to help seat the ligating bands onto support structure 14.

Figure 16:
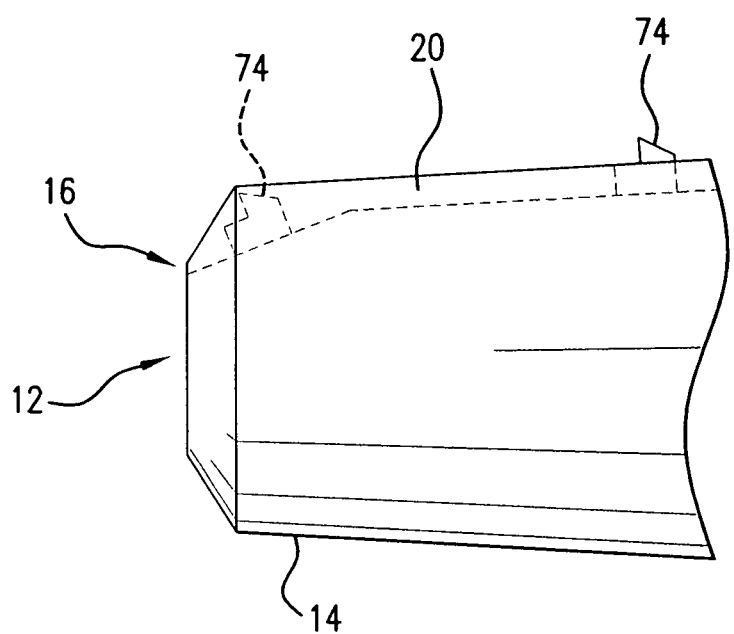
FIG. 16 is a side view of a distal portion of a ligating band dispenser according to another embodiment.

In yet another embodiment, the ligating band dispenser is adapted to reduce the outward projection of the sliding element from the surface of the support structure as the sliding element moves distally along the support structure. By reducing the sliding element's outward projection from the surface of the support structure, the sliding element may be concealed, hidden, sequestered, or otherwise have its external profile reduced. For example, as shown in FIG. 16, the distal portion of the groove 20 may increase in depth to allow sliding element 74 to become sequestered within support structure 14 as sliding element 74 is advanced distally. In some embodiments, groove 20 is configured so that sequestration of sliding element 74 occurs after the ligating band is deployed. In some embodiments, groove 20 is sloped downward such that sliding element 74 rotates forward after deployment of a ligating band. Where sliding element 74 is slotted, forward rotation may assisted in releasing the pull line.

The present invention has been described with respect to several exemplary embodiments. There are many modifications of the disclosed embodiments which will be apparent to those of skill in the art. It is understood that these modifications are within the teaching of the present invention which is to be limited only by the claims.

What is claimed is:

1. A ligating band dispenser comprising:
    a support structure having a channel, an outer surface, a proximal end, and a distal end;
    a groove on the outer surface of the support structure;
    at least one sliding element slidably engaged to the groove on the support structure, wherein the groove has a shoulder that projects laterally over the groove to retain the sliding element on the support structure as the sliding element slides within the groove;
    a pull line engaged with the at least one sliding element; and
    at least one ligating band positioned on the outer surface of the support structure distal to the at least one sliding element;
    wherein pulling the pull line causes the at least one sliding element to move distally with respect to the outer surface of the support structure, thereby causing the at least one ligating band to move distally with respect to the outer surface of the support structure and off of the distal end of the support structure; and
    wherein the sliding element is structured to disengage the pull line as the sliding element is drawn past the distal end of the support structure.

2. The ligating band dispenser of claim 1, wherein the support structure has an inner surface, wherein the inner surface of the support structure has a groove, and wherein the groove on the inner surface is continuous with the groove on the outer surface.

3. The ligating band dispenser of claim 1, wherein the groove extends along the outer surface of the support structure at an oblique angle to a central axis of the support structure.

4. The ligating band dispenser of claim 1, wherein the groove extends helically along the outer surface of the support structure.

5. The ligating band dispenser of claim 1, wherein the groove is adapted to reduce the outward projection of the sliding element from the outer surface of the support structure as the sliding element moves distally along the support structure.

6. The ligating band dispenser of claim 5, wherein at least one distal point on the groove is deeper than a proximal point on the groove.

7. The ligating band dispenser of claim 1, wherein the sliding element comprises a slot through which the pull line travels.

8. The ligating band dispenser of claim 7, wherein the slot is V-shaped.

9. The ligating band dispenser of claim 1, wherein the sliding element is formed of a material that is biodegradable within a body.

10. The ligating band dispenser of claim 1, wherein the sliding element is formed of a material that is absorbable by a body.

11. The ligating band dispenser of claim 1, wherein the sliding element rotates as the sliding element moves distally along the support structure.

12. The ligating band dispenser of claim 1, wherein the support structure further comprises at least one circumferential furrow that extends at least partially around the support structure.

13. The ligating band dispenser of claim 1, wherein the shoulder retains the sliding element within the groove.

14. A ligating band dispenser comprising:
    (a) a support structure having a channel, a proximal end, a distal end, an outer surface, and a groove on an outer surface of the support structure;
    (b) at least one ligating band positioned on the outer surface of the support structure;
    (c) a pull line adapted to be pulled proximally for deploying the at least one ligating band off of the distal end of the support structure; and
    (d) a means for moving the at least one ligating band distally, wherein the means for moving the at least one ligating band distally is slidably engaged to the groove on the support structure, wherein the groove has a laterally-projecting shoulder that projects laterally over the groove to retain the means for moving on the support structure as the means for moving slides within the groove, and wherein the means for moving the at least one ligating band distally disengages the pull line after deployment of the at least one ligating band.

15. The ligating band dispenser of claim 14, wherein the means for moving the at least one ligating band distally comprises at least one sliding element.

16. The ligating band dispenser of claim 14, wherein the means for moving is formed of a material that is biodegradable within a body.

17. The ligating band dispenser of claim 14, wherein the means for moving is formed of a material that is absorbable by a body.

18. A device for deploying a ligating band, comprising:
    a support structure having a groove on an outer surface thereof;
    a pushing element slidably engaged to the groove on the support structure, wherein the groove has a shoulder that projects laterally over the groove to retain the pushing element on the support structure as the pushing element slides within the groove;
    an actuating element for moving the pushing element;
    a ligating band seated adjacent to the pushing element;
    wherein actuation of the actuating element causes the pushing element to push against the ligating band and move the ligating band distally along the support structure; and
    wherein the pushing element is structured to disengage the actuating element as the sliding element is drawn past a distal end of the support structure.

19. The device of claim 18, wherein the actuating element comprises a pull line.

20. The device of claim 18, wherein the shoulder retains the pushing element within the groove.

21. A method of dispensing ligating bands, comprising the steps of:
    (a) using a ligating dispenser of claim 1; and
    (b) pulling the pull line proximally, thereby causing the at least one sliding element to move distally with respect to the outer surface of the support structure, thereby causing the at least one ligating band to move distally with respect to the outer surface of the support structure and off of the distal end of the support structure.

22. The method of claim 21, further comprising the step of agitating the sliding element to thereby cause the sliding element to disengage from the pull line.

23. The method of claim 21, further comprising the step of rotating the sliding element to thereby cause the sliding element to disengage from the pull line.

\* \* \* \* \*